US005423883A

United States Patent [19]
Helland

[11] Patent Number: 5,423,883
[45] Date of Patent: Jun. 13, 1995

[54] IMPLANTABLE MYOCARDIAL STIMULATION LEAD WITH SENSORS THEREON

[75] Inventor: John R. Helland, Santa Clarita, Calif.

[73] Assignee: Pacesetter, Inc., Sylmar, Calif.

[21] Appl. No.: 91,851

[22] Filed: Jul. 14, 1993

[51] Int. Cl.⁶ .............................................. A61N 1/05
[52] U.S. Cl. .................................. 607/127; 128/642; 607/18
[58] Field of Search ............... 607/126, 127, 129, 130, 607/131, 132, 18; 128/642

[56] References Cited

U.S. PATENT DOCUMENTS 4,010,758  3/1977  Rockland et al. .
4,355,642 10/1982  Alferness ............................ 128/642
5,109,842  5/1992  Adinolfi .
5,154,175 10/1992  Gunther ............................. 128/642
5,154,183 10/1992  Kreyenhagen et al. ........... 607/131

Primary Examiner—William E. Kamm
Assistant Examiner—Scott M. Getzow
Attorney, Agent, or Firm—Lisa P. Weinberg

[57] ABSTRACT

A myocardial lead is provided with at least one sensor for sensing at least one of heart rate, physiological demand, or arrhythmia. Preferably, the sensor is a piezoelectric crystal, and is designed to flex with the beating of the human heart. Other suitable sensors include accelerometers, hemo-reflectance sensors, and strain gauge sensors. Each sensor is provided on a separate conductive segment of the electrode assembly. The signals can be monitored by appropriate electronics to detect changes in heart rate or arrhythmias of the heart.

28 Claims, 2 Drawing Sheets

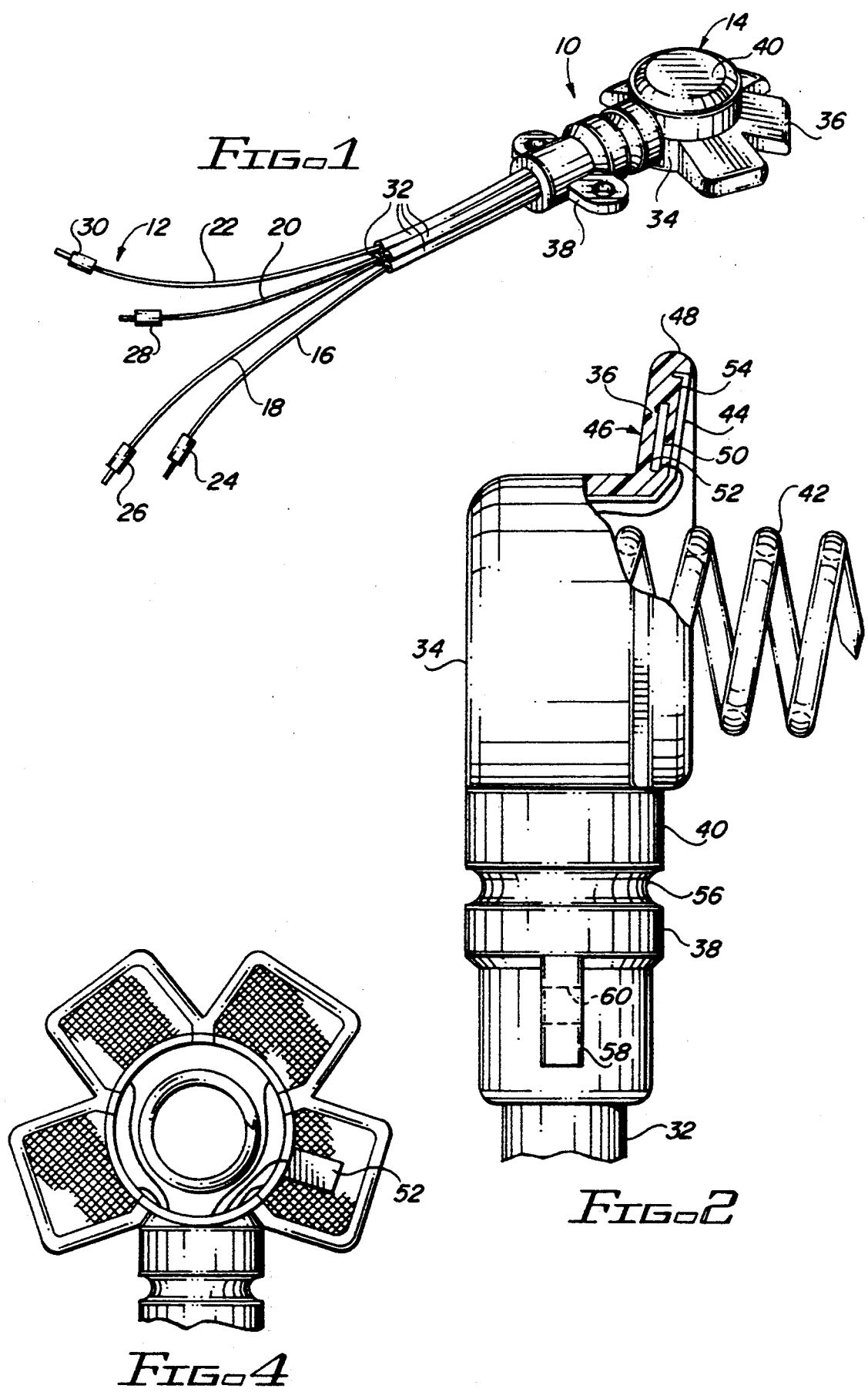

IMPLANTABLE MYOCARDIAL STIMULATION LEAD WITH SENSORS THEREON

FIELD OF THE INVENTION

The present invention relates to an implantable myocardial lead for an implantable tissue stimulator and, more specifically, to a myocardial lead having sensors mounted thereon for detecting cardiac arrhythmias.

BACKGROUND OF THE INVENTION

Myocardial leads have electrodes which are attached to the exterior of a human heart and deliver stimulation pulses from an implanted cardiac pacemaker to a patient's heart. The myocardial leads are attached to the heart typically by positively fixating a distal electrode into the myocardial tissue. A skirt portion located behind the electrode typically is used for passive tissue ingrowth. Generally, it is preferable to use two myocardial leads, for stimulating in a bipolar fashion, to prevent inadvertent stimulation of skeletal muscle tissue or other tissue during cardiac pacing.

One such myocardial lead is discussed in U.S. Pat. No. 5,154,183 (Kreyenhagen et al.), which reference is hereby incorporated herein by reference. The myocardial lead includes a center section and a number of leaf-shaped appendages, or petals, extending outwardly from the center section. The center section has a positive fixation electrode made of electrically conductive material. The leaf-shaped appendages are securely connected to the center section and extend radially outward from the center section.

Each leaf-shaped appendage includes at least one conductive segment. The conductive segments on the leaf-shaped appendages are also electrically insulated from the first member on the center section. The leaf-shaped appendages conform to the heart's surface, flex to insure reliable contact with the heart tissue, and will maintain contact during both heart contractions and rest periods. The leaf-shaped appendages may be electrically connected together to act as a second electrode for bipolar sensing, or may be individually used as separate electrodes in a multipolar fashion.

Many types of implantable systems are known for tachyarrhythmia control. Such systems have gained greater acceptance in recent years as an alternative therapy to chronic pharmacologic treatment. Such tachyarrhythmia control systems typically include an implantable device capable of tachyarrhythmia detection and delivery of an automatic therapeutic response to the arrhythmia, including bradycardia pacing support, anti-tachyarrhythmia pacing, low energy synchronized cardioversion or high energy defibrillation shock, an electrode system for sensing and pacing, and a high energy electrode system for delivery of defibrillation shock. Typically the pacing and sensing electrode system will consist of a bipolar endocardial lead or two unipolar myocardial leads. The high energy electrode system generally consists of two myocardial patch leads, or a transvenous shocking lead with either a myocardial or subcutaneous patch lead.

Any device that is intended to provide automatic treatment of ventricular tachyarrhythmias must be capable of first detecting the presence of such arrhythmias prior to the onset of therapy. Several methods are known for detecting ventricular tachyarrhythmias. These include monitoring an absolute heart rate interval, and initiating therapy when the interval becomes less than a programmable interval threshold.

It is also known to try to differentiate pathologic rhythms from normal physiologic rhythms by analyzing the rate of onset (sudden change, as opposed to gradual change in the heart rate interval) and/or heart rate stability.

It is also known to determine the probability density function of a signal corresponding to heart activity, which involves the evaluation of the time that the cardiac electrical signal spends at an isoelectric base line, and to initiate therapy when deviations beyond a predetermined threshold occur.

The known detection techniques have several limitations and disadvantages. The two major disadvantages are (1) no accurate method of differentiating between a pathologic (i.e. hemodynamically compromising) rhythm versus a physiologic (i.e., sinus) rhythm, and (2) total reliance on a processed electrogram for detection of cardiac depolarization. As a result of the second disadvantage, certain rhythms, particularly low amplitude ventricular fibrillation, may not be detected. These limitations in the known detection techniques may result either in a false positive detection response (inappropriate shock delivery) or a false negative detection response (failure to respond to a pathologic rhythm).

SUMMARY OF THE INVENTION

In accordance with the principles of the present invention, an improved myocardial lead is provided with at least one sensor embedded therein for generating signals corresponding to cardiac heart wall motion and/or physiological demand.

The present invention is achieved by securing at least one sensor to a skirt electrode, typically a mesh electrode, of a myocardial lead. In the preferred embodiment, the skirt electrode comprises a plurality of leaf-shaped appendages which can be angled slightly forward to conform to the heart muscle. The sensor can be secured either on a surface of one of the leaf-shaped appendages or within the leaf-shaped appendage of the myocardial lead.

A suitable sensor, such as a piezoelectric crystal, can be designed to flex with the beating of a human heart when secured to the leaf-shaped appendage of the myocardial lead. The flexing then generates electrical signals that can be monitored by appropriate electronics. These signals indicate when the heart is in tachycardia, fibrillation, or any other arrhythmia.

The output of the sensor is processed and monitored by the implantable device to determine the extent of the wall motion, the cardiac energy, and/or the frequency of myocardial motion and to determine and differentiate the specific myocardial rhythm of an individual patient. The sensor can be used as a primary or secondary indicator of the onset of ventricular tachyarrhythmias, including ventricular fibrillation in a conventional implantable defibrillating system.

The system operates based on the knowledge that in a normal physiologic cardiac rhythm, electrical depolarization and subsequent myocardial wall motion follows a specific pattern and sequence, and that an effective myocardial systole will result in a recognizable, identifiable myocardial excursion and energy. A pathologic (hemodynamically compromising) cardiac rhythm, by contrast, will result in an ineffective and/or chaotic cardiac wall motion. Monitoring of the excursion of the cardiac wall and the energy associated with the sensor signal permits discrimination between pathologic and physiologic rhythms.

In alternate embodiments, a sensor could be used to maintain rate adaptation or for treating arrhythmias of the human heart. For example, other suitable sensors include, but are not limited to, mechanical cardiac activity sensors (such as piezoelectric crystals, accelerometers or other motion sensors) for detecting heart wall motion; hemo-reflectance sensors that measure a desired characteristic of the heart tissue (such as blood pressure or heart rate); and strain gauge sensors configured to measure contractility or blood pressure.

DESCRIPTION OF THE DRAWINGS

Further features and advantages of the present invention may be more readily understood by reference to the following description taken in conjunction with the accompanying drawings, in which:

FIG. 1 illustrates a perspective view of a myocardial lead, constructed in accordance with the principles of the present invention;

FIG. 2 illustrates a side view of the distal end of an electrode assembly of the myocardial lead, shown in FIG. 1, including a partial cutaway section;

FIG. 4 illustrates a front view of a distal end of the electrode assembly using a single sensor (52)

DETAILED DESCRIPTION OF THE PREFERRED EMBODIMENT

Figure 3:
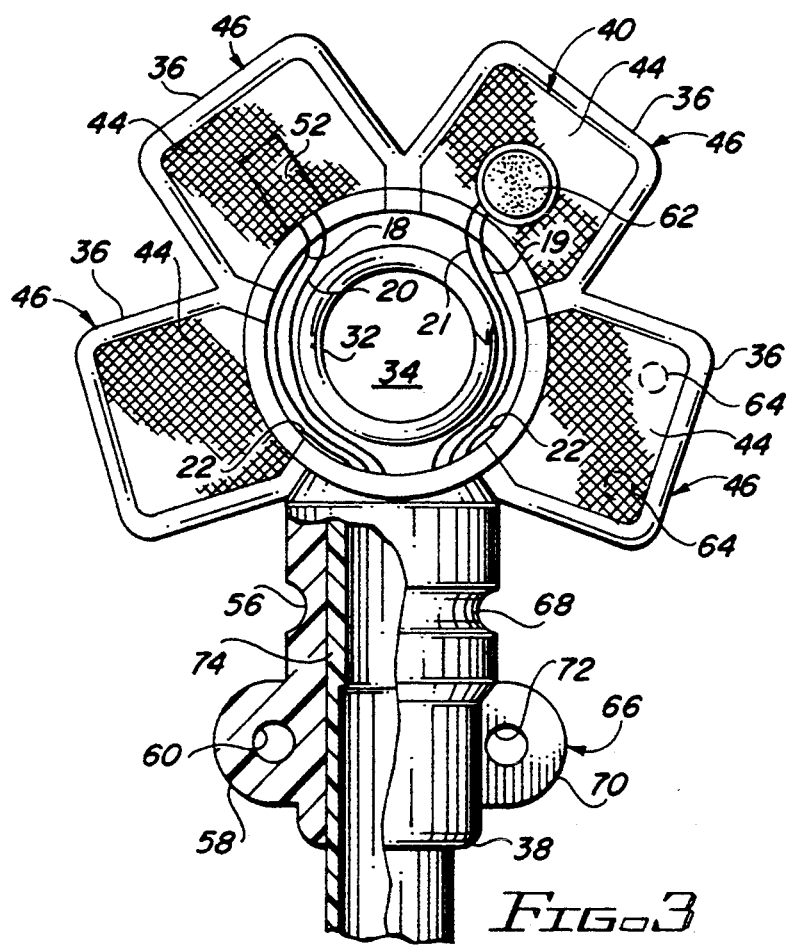
FIG. 3 illustrates a front view of a distal end of the electrode assembly of the myocardial lead, shown in FIG. 1, illustrating the location of the sensors (52, 62) and including a partial cutaway section.

FIG. 1 illustrates a multipolar myocardial electrode assembly 10 (i.e., an electrode having multiple appendages wherein each appendage may used separately for sensing or pacing) constructed in accordance with the principles of the present invention. While a multipolar myocardial electrode is shown, it is for illustrative purposes only, since the present invention could be practiced using any number of appendages. The assembly 10 includes a proximal end 12 and a distal end 14. Four conductors 16, 18, 20 and 22, extend between the proximal end 12 and the distal end 14. The conductors 16, 18, 20 and 22 are terminated at the proximal end 12 by connectors 24, 26, 28 and 30, respectively.

A suitable insulative casing 32 is provided for each of the conductors 16, 18, 20 and 22. The insulative casing may be constructed using multilumen technology and is well known in the art. Alternately, the conductors 16, 18, 20, 22 may be individually coated with a thin polymer coating, such as polyimide and coiled in a multifilar fashion, as is also known in the art. The insulative casing 32 is constructed from a suitable insulative material, such as silicone rubber. However, any suitable type of insulative medical-grade material, which is biocompatible and biostable, may be used. The length of the conductors 16, 18, 20 and 22 will be similar to the length of conventional myocardial leads.

The distal end 14 of the assembly 10 includes a center section, or hub section, 34, an insulative backing section 36 and an anchoring section 38. Preferably, the distal end 14 has a housing 40 which may be configured, as illustrated in FIG. 1, or in a similar configuration. The housing 40, the insulative backing section 36, and the anchoring section 38 are formed of a suitable insulating material, such as silicone rubber. However, any suitable type of insulative medical-grade material may be used.

As illustrated in FIG. 2, a positive fixation electrode 42 and a number of conductive appendages 44 (illustrated in FIG. 3) are fixedly mounted together with the housing 40. The positive fixation electrode 42 is formed of a relatively rigid, biocompatible and biostable electrically conductive material, such as platinum-iridium. In a preferred embodiment, the positive fixation electrode 42 is shaped in the form of a screw-in helix. Other configurations of the positive fixation electrode 42 can also be utilized without departing from the principles of the present invention. For example, a barbed hook, a staple, or other tissue positive fixation arrangements could also be used. The positive fixation electrode 42 is electrically connected to the lead 16 (illustrated in FIG. 1), and forms a first electrode which may be screwed into the heart tissue of a patient.

The conductive appendages 44 (illustrated in FIG. 3) extend radially outward from the center section 34 of the assembly 10, as illustrated in FIG. 2. The conductive appendages 44 are in a plane approximately perpendicular to the axis of the positive fixation electrode 42. In a preferred embodiment, the conductive appendages 44 will be flexed forward to embrace the tissue of the heart, and will flex forward and backward to move with the tissue of the heart.

The conductive appendages 44, together with the insulative backing section 36, form four leaf-shaped appendages, or petals, 46 (illustrated in FIG. 3). An edge, or bead, 48, which is part of the insulative backing section 36, is located at outer edges of the four leaf-shaped appendages 46. The edge 48 is rounded to prevent irritation of the heart tissue. A sensor 52 is preferably housed in a hermetic case to seal out bodily fluids. The sensor 52 may be molded within the insulative backing section 36 and then electrically isolated from the conductive appendages 44. In an alternate embodiment, the sensor 52 can be secured to either an exterior or interior surface of the conductive appendages 44.

The sensor 52 can be used to monitor a variety of physiological functions, such as heart rate, blood pressure, contractility and arrhythmias. Any suitable sensor can be used for the purpose of maintaining rate adaptation or for treating arrhythmias of the human heart. For example, other suitable sensors include, but are not limited to, mechanical cardiac activity sensors (such as piezoelectric crystals and accelerometers) for detecting heart wall motion; hemo-reflectance sensors that measure a desired characteristic of the heart tissue (such as blood pressure and heart rate); and strain gauge sensors (configured, for example, to measure contractility or blood pressure).

An annular groove 56 (FIGS. 2 and 3) is provided around the anchoring section 38 for securing the lead to the heart tissue with sutures. Optionally, an eyelet section 58 having a suture aperture 60 is provided on the distal end 14 of the assembly 10. The insulative casings 32 then extend from the distal end 14 to the proximal end 12 of the assembly 10. The anchoring section 38 can be molded onto or otherwise attached to the lead adjacent to the distal end 14, or may be slidably attached so that it can be moved along the lead body to a site more preferred by the physician for anchoring the lead.

As illustrated in FIG. 3, the leaf-shaped appendages 46 include the conductive appendages 44 and a portion of the housing 40 extending to the insulative backing section 36. The positive fixation electrode 42 is connected to conductor 16 to form a first electrode. The sensor 52 typically has two terminals connected to conductors 18 and 20. The remaining conductive appendages 44, without sensors, may be connected to conductor 22 to form a second electrode.

A second sensor 62 may also be used. The second sensor 62 may be molded in the insulative backing section 36, or, as shown in FIG. 3, may be disposed on an exterior surface 64 of one of the conductive appendages 44. Any suitable sensor can be used as the second sensor 62, as described above in conjunction with sensor 52. If the second sensor 62 is employed, additional conductors 19 and 21 (not shown in FIG. 1) will be required. For a complete description of the advantages of using two or more sensors and the control circuitry to process those signals. See copending U.S. patent application, entitled "Implantable Leads Incorporating Cardiac Wall Motion Sensors and Method of Fabrication and a System and Method for Detecting Cardiac Arrhythmias Using a Cardiac Wall Motion Sensor Signal," filed concurrently herewith, which application is hereby incorporated herein by reference.

Although FIG. 3 illustrates four leaf-shaped appendages 46 and two sensors 52, 62, an arrangement including only one sensor (illustrated in FIG. 4), or an arrangement including multiple sensors (not illustrated) can be provided. Further, any suitable number of leaf-shaped appendages 46 can be provided in order to accommodate a number of sensors and/or a number of additional electrodes.

Conductors 16, 18, 20 and 22 can be connected to the positive fixation electrode 42, the two terminals for sensor 52 (or 62), and the remaining conductive appendages 44, respectively, in either the anchoring section 38 or within the hub section 34. By providing an additional mechanical arrangement for connecting the anchoring section 34 to the heart tissue, the risk of a faulty connection or damage to the leads at the distal end 14 is decreased.

The conductive appendages 44 extend radially outward from the hub section 34, and are in a plane approximately perpendicular to the axis of the positive fixation electrode 42 (illustrated in FIG. 2). The leaf-shaped appendages 46 extend radially outward relative to the center axis of the positive fixation electrode 42 in a substantially perpendicular fashion, but are angled slightly forward (as illustrated in FIG. 2) to form a generally frustroconical shape. Preferably, the leaf-shaped appendages 46 are moderately flexible, such that when the distal end 14 is screwed into a patient's heart by the positive fixation electrode 42, the leaf-shaped appendages 46 can contact the surface of the heart and flex back slightly to provide constant and conformal intimate contact with the heart and flex with movement of the heart tissue. The leaf-shaped appendages 46 can also be provided with apertures 64, such that sutures (not illustrated) may be passed through the apertures 64 to fixedly connect the leaf-shaped appendages 46 to the heart tissue.

Each of the conductive appendages 44 are electrically isolated from one another. However, the conductive appendages 44 can be electrically connected to one another. Further, each of the remaining conductive appendages 44 can be connected to separate leads, rather than to the single lead 22, as illustrated in FIG. 3. Thus, a pacemaker (not illustrated) could individually address each of the conductive appendages 44, and selectively use any or all of the conductive appendages 44 for pacing and/or for sensing.

As further illustrated in FIG. 3, the anchoring section 38 includes an eyelet section 66 and a suture groove section 68. The eyelet section 66 includes two laterally extending sections 58, 70 with suture apertures 60, 72. Suture apertures 60, 72 can be used to fixedly connect the anchoring section 38 of the housing 40 to the heart tissue. However, the eyelet section 66 is optional, and need not be provided.

The suture groove section 68 includes an annular groove 56 around the anchoring section 38, and a compression protection member 74. The compression protection member 74 prevents the insulative casing 32 of conductors 16, 18, 20, and 22 from being damaged when the suture is tightly tied. In a preferred embodiment, the protection member 74 is made of hard plastic. However, any mechanically suitable material can be used to form the protection member 74. In an alternate embodiment, the entire anchoring section can be eliminated and not used.

In addition to functioning as pacing electrodes, the conductive appendages 44 are preferably formed of a conductive porous or mesh material, and are configured to promote rapid tissue ingrowth into the electrode material, the space 52 and around the leaf-shaped appendages 46.

FIG. 4 illustrates a single sensor 52 secured to an exterior surface 64 of one of the conductive appendages 44. The remaining conductive appendages 44 are all connected to a single lead. Thus, only four leads are necessary in accordance with the embodiment illustrated in FIG. 4 to individually connect the positive fixation electrode 42, the sensor 52, and the remaining conductive appendages 44.

Figure 5:
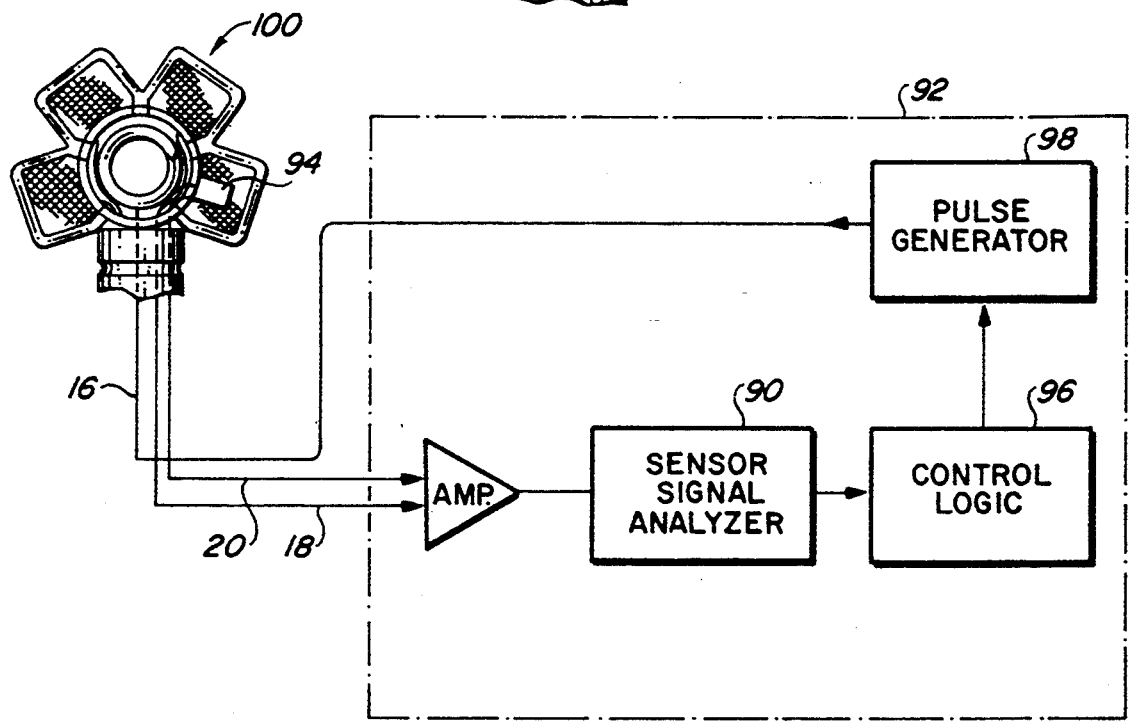
FIG. 5 is a schematic block diagram of an implantable pulse generator system constructed in accordance with the principles of the present invention using the myocardial electrode shown in FIG. 4.

As is shown in FIG. 5, a signal analyzer 90 located within an implantable pulse generator 92 will analyze one or more characteristics of the sensor signal, such as amplitude, frequency, energy content, etc., and will generate an output signal if one or a selected combination of these characteristics deviates from a predetermined threshold. For example, the chaotic cardiac wall motion which occurs during ventricular fibrillation will cause a piezoelectric sensor 94 located on the myocardial lead 10 to produce amplitude excursions which would be dramatically different than the amplitude and/or frequencies which will be present during normal cardiac activity.

Upon the detection of a particular characteristic, or set of characteristics, indicating abnormal cardiac activity, the sensor signal analyzer 90 will supply a signal to control logic 96 or microprocessor (not shown) within the implantable pulse generator 92, as is known in the art. The sensor signal may be used as a primary indicator of the onset of fibrillation or ventricular tachycardia, or may be used as a confirmation of the occurrence of fibrillation or ventricular tachycardia which has been detected by one of the aforementioned known techniques. In the event of an identification or confirmation of the onset of fibrillation or ventricular tachycardia based on the output of the sensor signal, the control logic 96 will enable the pulse generator 98 to determine the appropriate action to be taken. For a complete description of an implantable arrythmia detection and control system, see U.S. Pat. No. 5,109,842, which patent is assigned to the same assignee as the present invention, and which patent is hereby incorporated herein by reference.

In alternate embodiments, the sensor could be used to maintain rate adaptation or to treat arrhythmias of the human heart. For example, other suitable sensors include, but are not limited to, mechanical cardiac activity sensors (such as piezoelectric crystals, accelerometers or other motion sensors) for detecting heart wall motion; reflectance (photoelectric) or impedance plethysmographic sensors that measure a desired characteristic of the heart tissue (which can be used to determine such parameters as blood pressure or heart rate); and strain gauge sensors configured to measure, for example, contractility or blood pressure. Thus, the sensors improve the detection of physiological data.

Although various minor modifications may be suggested by those versed in the art, it should be understood that I wish to embody within the scope of the patent granted hereon all such modifications as reasonably and properly come within the scope of my contribution to the art.

What is claimed is:

1. A myocardial lead for use with an implantable stimulation device comprising:

a positive fixation electrode having a proximal end and a distal end, the distal end of the positive fixation electrode being adapted for connecting to heart tissue;

electrogram sensing means, coupled to the positive fixation electrode, for sensing cardiac signals;

a nonconductive hub member, the proximal end of the positive fixation electrode being received in the hub member;

an appendage connected to and extending radially outward from the hub member, the appendage having a segment of conductive material electrically insulated from the positive fixation electrode, each segment of conductive material having a first surface adapted for contacting heart tissue and a second surface having insulating means thereon, the insulating means being connected to the hub member;

physiological sensing means, secured to the appendage, for sensing a physiological parameter of the body corresponding to at least one of arrhythmias, physiological demand or heart rate of a human heart; and conductive means for electrically connecting the positive fixation electrode and the physiological sensing means to the implantable stimulation device.

2. A myocardial lead, as claimed in claim 1, wherein the physiological sensing means comprises a plurality of physiological sensors.

3. A myocardial lead, as claimed in claim 2, wherein the appendage comprises a plurality of leaflets, each leaflet having one of the plurality of physiological sensors mounted thereon.

4. A myocardial lead, as claimed in claim 1, wherein the physiological sensing means is molded in the insulating means of the appendage.

5. A myocardial lead, as claimed in claim 1, wherein the physiological sensing means is secured to the first surface adapted for contacting heart tissue.

6. A myocardial lead, as claimed in claim 1, wherein the physiological sensing means is disposed between the insulating means and the second surface of the conductive material.

7. A myocardial lead, as claimed in claim 1, wherein the physiological sensing means is a mechanical cardiac activity sensor.

8. A myocardial lead, as claimed in claim 1, wherein the physiological sensing means is a piezoelectric sensor.

9. A myocardial lead, as claimed in claim 1, wherein the physiological sensing means is an accelerometer.

10. A myocardial lead, as claimed in claim 1, wherein the physiological sensing means is a hemo-reflectance sensor which measures a desired characteristic of the heart tissue.

11. A myocardial lead, as claimed in claim 10, wherein the desired characteristic of the heart tissue is blood pressure.

12. A myocardial lead, as claimed in claim 10, wherein the desired characteristic of the heart tissue is heart rate.

13. A myocardial lead, as claimed in claim 1, wherein the physiological sensing means is a strain gage sensor which measures a desired characteristic of the heart tissue.

14. A myocardial lead, as claimed in claim 13, wherein the desired characteristic of the heart tissue is contractility.

15. A myocardial lead as claimed in claim 13, wherein the desired characteristic of the heart tissue is blood pressure.

16. A myocardial lead for use with an implantable stimulation device comprising:

a positive fixation electrode having a proximal end and a distal end, the distal end of the positive fixation electrode being adapted for connecting to heart tissue;

electrogram sensing means, coupled to the positive fixation electrode, for sensing cardiac signals;

a nonconductive electrode body, the proximal end of the positive fixation electrode being received in the electrode body;

a skirt electrode connected to and extending radially outward from the electrode body, the skirt electrode having a segment of conductive material electrically insulated from the positive fixation electrode, each segment of conductive material having a first surface adapted for contacting heart tissue and a second surface having insulating means thereon, the insulating means being connected to the electrode body;

at least one physiological sensor secured to the skirt electrode for sensing at least one of arrhythmias, physiological demand or heart rate of a human heart; and a lead body having a proximal end and a distal end and conductive means therebetween, the positive fixation electrode being electrically connected at the distal end of the lead body, and the proximal end having a connector for connecting the positive fixation electrode and the physiologic sensor to the implantable stimulation device.

17. A myocardial lead, as claimed in claim 16, wherein the at least one physiologic sensor comprises a plurality of physiologic sensors.

18. A myocardial lead, as claimed in claim 17, wherein the skirt electrode comprises a plurality of leaflets, each leaflet having one of the plurality of physiologic sensors mounted thereon.

19. A myocardial lead, as claimed in claim 16, wherein the at least one physiologic sensor is molded in the insulating means of the skirt electrode.

20. A myocardial lead, as claimed in claim 16, wherein the at least one physiologic sensor is secured to the first surface adapted for contacting heart tissue.

21. A myocardial lead, as claimed in claim 16, wherein the at least one physiologic sensor is disposed between the insulating means and the second surface of the conductive material.

22. A myocardial lead, as claimed in claim 16, wherein the at least one physiologic sensor is a mechanical cardiac activity sensor.

23. A myocardial lead, as claimed in claim 16, wherein the at least one physiologic sensor is a piezoelectric sensor.

24. A myocardial lead, as claimed in claim 16, wherein the at least one physiologic sensor is an accelerometer.

25. A myocardial lead, as claimed in claim 16, wherein the at least one physiologic sensor is a hemoreflectance sensor which measures a desired characteristic of the heart tissue.

26. A myocardial lead, as claimed in claim 16, wherein the at least one physiological sensor is a strain gage sensor which measures a desired characteristic of the heart tissue.

27. A myocardial lead, as claimed in claim 25, wherein the desired characteristic of the heart tissue is either blood pressure or heart rate.

28. A myocardial lead, as claimed in claim 26, wherein the desired characteristic of the heart tissue is either contractility or blood pressure.

* * * * *